United States Patent [19]
Geng

[11] Patent Number: 6,043,408
[45] Date of Patent: Mar. 28, 2000

[54] WOUND DRESSING HAVING A MOVABLE FLAP FOR ALTERNATELY VIEWING AND COVERING A WOUND

[76] Inventor: Lisa Fernandez Geng, 79 Kerrigan St., Long Beach, N.Y. 11561

[21] Appl. No.: 08/650,088

[22] Filed: May 17, 1996

Related U.S. Application Data

[60] Continuation of application No. 08/472,119, Jun. 7, 1995, abandoned, which is a division of application No. 08/289,845, Aug. 12, 1994, abandoned, which is a continuation of application No. 08/056,733, May 4, 1993, abandoned.

[51] Int. Cl.[7] .................................................. A61F 13/00
[52] U.S. Cl. ................................ 602/58; 602/54; 602/57
[58] Field of Search ........................ 602/41–59; 128/887, 128/888, 889; 604/180, 174, 304–308

[56] References Cited

U.S. PATENT DOCUMENTS

| | | |
|---|---|---|
| 2,633,128 | 3/1953 | Schaefer . |
| 3,262,277 | 7/1966 | Nesbitt . |
| 3,367,329 | 2/1968 | Dibelius . |
| 3,425,412 | 2/1969 | Pope . |
| 3,826,253 | 7/1974 | Larsh et al. . |
| 4,091,809 | 5/1978 | Cortner, Jr. et al. . |
| 4,399,816 | 8/1983 | Spangler . |
| 4,513,739 | 4/1985 | Johns . |
| 4,641,643 | 2/1987 | Greer ........................................ 602/58 |
| 4,649,909 | 3/1987 | Thompson . |
| 4,655,210 | 4/1987 | Edenbaum et al. . |
| 4,655,980 | 4/1987 | Chu . |
| 4,706,662 | 11/1987 | Thompson . |
| 4,711,781 | 12/1987 | Nick et al. . |
| 4,737,400 | 4/1988 | Edison et al. . |
| 4,776,331 | 10/1988 | Simjian . |
| 4,917,112 | 4/1990 | Kalt . |
| 4,981,133 | 1/1991 | Rollband . |
| 5,009,224 | 4/1991 | Cole . |
| 5,086,763 | 2/1992 | Hathman ................................. 602/42 |
| 5,127,423 | 7/1992 | Draeger . |
| 5,149,469 | 9/1992 | Komatsuzaki et al. . |
| 5,167,613 | 12/1992 | Karami et al. . |
| 5,244,523 | 9/1993 | Tollini . |
| 5,449,340 | 9/1995 | Tollini ..................................... 602/58 |
| 5,520,629 | 5/1996 | Heinecke et al. . |

*Primary Examiner*—Kim M. Lee
*Attorney, Agent, or Firm*—Pennie & Edmonds LLP

[57] ABSTRACT

An external wound dressing having a cover which is reversibly movable to an open position exposing the wound from a closed position covering the wound thereby enabling selective viewing of the wound without removing the wound dressing from the individual.

33 Claims, 3 Drawing Sheets

WOUND DRESSING HAVING A MOVABLE FLAP FOR ALTERNATELY VIEWING AND COVERING A WOUND

This is a continuation, of application Ser. No. 08/472,119, filed Jun. 7, 1995, now abandoned, which is a divisional of application Ser. No. 08/289,845, filed: Aug. 12, 1994 now abandoned, which is a continuation of application Ser. No. 08/056,733, filed: May 4, 1993, now abandoned.

FIELD OF THE INVENTION

The present invention is generally directed to a wound dressing and particularly to a wound dressing which enables the wound to be viewed by a person such as patient, doctor, mother, child, etc. without removing the wound dressing. A cover means, particularly in the form of a flap, is provided which is movable to an open position to allow viewing of the wound from a closed position whereby viewing of the wound is prevented.

BACKGROUND OF THE INVENTION

Wound dressings, including Band-Aid® brand wound dressings, generally include an opaque backing layer having an adhesive applied to one side for adhering to the skin. A protective layer, typically made of a release paper is applied to the adhesive side of the backing layer and is releasable therefrom when the wound dressing is applied to the skin. The area immediately covering the wound often has a gauze pad which may be impregnated with an antibacterial agent or the like.

Wound dressings as described above and as disclosed, for example, in N. R. Dibelius, U.S. Pat. No. 3,367,329, must be removed in order for the individual and/or the physician to view the wound. Once the wound dressing is removed it may become contaminated or difficult to put back on the wound. Therefore, removal of the wound dressing often necessitates replacing the old wound dressing with a new one, which can be stressful to the individual.

Excessive use of wound dressings is also apparent when young children obtain superficial wounds such as minor cuts, abrasions and the like. Children are naturally curious and they often prematurely remove a wound dressing to view their wound and to show it to their friends. Each time a wound dressing is removed, it is often difficult to reapply the same wound dressing because the adhesive layer loses its tackiness and the like. Accordingly, the number of wound dressings used during the healing of minor cuts and abrasions, particularly with children, is often greater than what might otherwise be expected.

A wound dressing was developed which enables the wound to be viewed without removing the wound dressing. In particular, O. L. Johns, U.S. Pat. No. 4,513,739, discloses an external wound dressing which may have a backing material made entirely out of a transparent polyurethane film. When the wound dressing is applied to the skin, the wound is always visible. While such a wound dressing enables the individual to view the wound without removing the dressing, permanent visibility has its disadvantages.

In particular, many individuals do not want to see their wound. In some cases, the wound is unpleasant to look at. Indeed, some individuals find the viewing of particularly onerous wounds very stressful and unpleasant and, therefore, would prefer wound dressings which completely hide the wound from view. As a result, the individual and/or physician must decide between opaque wound dressings which do not allow the wound to be viewed in the absence of removing the wound dressing, and transparent wound dressings in which the wound is permanently open to view. Quite obviously, each such wound dressing has its disadvantages.

It would be a significant advance in the wound dressing industry to provide a wound dressing in which (a) the wound could be viewed by the individual and/or physician without removing the wound dressing and (b) the wound could be covered when the viewing of the wound is not desired.

SUMMARY OF THE INVENTION

The present invention is generally directed to a wound dressing which permits selective viewing of a wound without having to remove the wound dressing from the skin. When viewing of the wound is completed, the wound may be covered by the individual or physician if desired and then viewed again at a later time without reapplying an entirely new wound dressing.

More particularly, one embodiment of the present invention is directed to an external wound dressing comprising:

(a) a first layer comprising a backing sheet material having a first portion for positioning over the wound and a second portion, said first portion being made of a material which enables the wound to be seen through the first layer;

(b) an adhesive on a first face of at least the second portion of the first layer of backing sheet material;

(c) a second layer comprising a protective sheet material covering the first layer and being in releasable contact with the adhesive, said second layer being removable from the adhesive to enable the wound dressing to be applied to the wound; and (d) cover means covering the first portion of the first layer and being reversibly movable from a closed position covering the wound to an open position so that the wound can be viewed by the user.

In an alternative embodiment, the first portion comprises an opening in the backing sheet material through which the wound may be seen when the cover means is moved to the open position.

BRIEF DESCRIPTION OF THE DRAWINGS

The following drawings in which like reference characters indicate like parts are illustrative of embodiments of the invention and are not intended to limit the invention as encompassed by the claims forming part of the application.

DETAILED DESCRIPTION OF THE INVENTION

Figure 1:
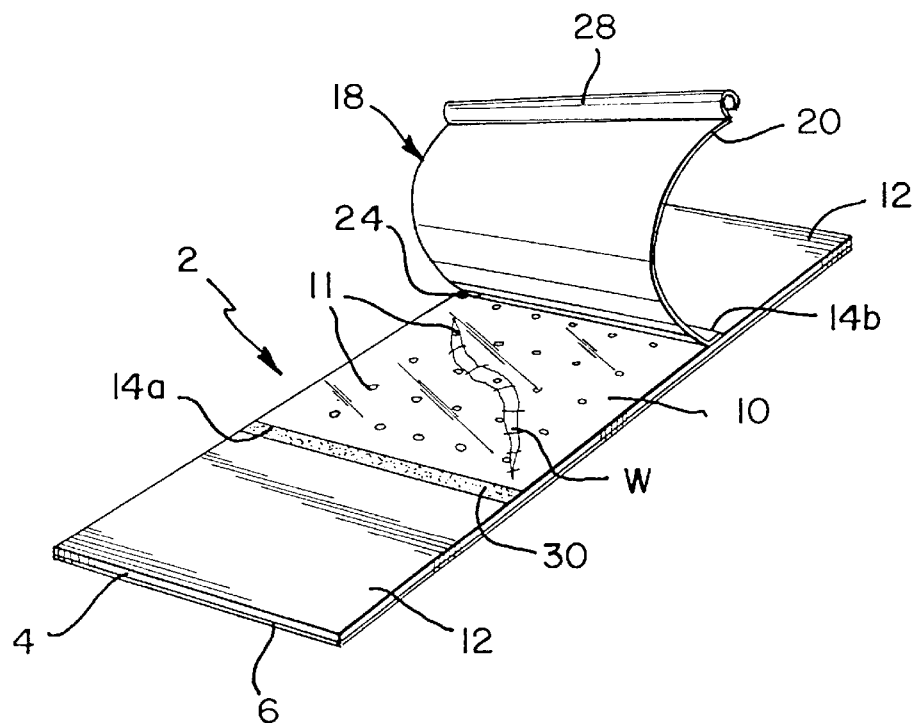
FIG. 1 is a perspective view of one embodiment of a wound dressing in accordance with the present invention with a flap in the open position for viewing the wound.
Figure 2:
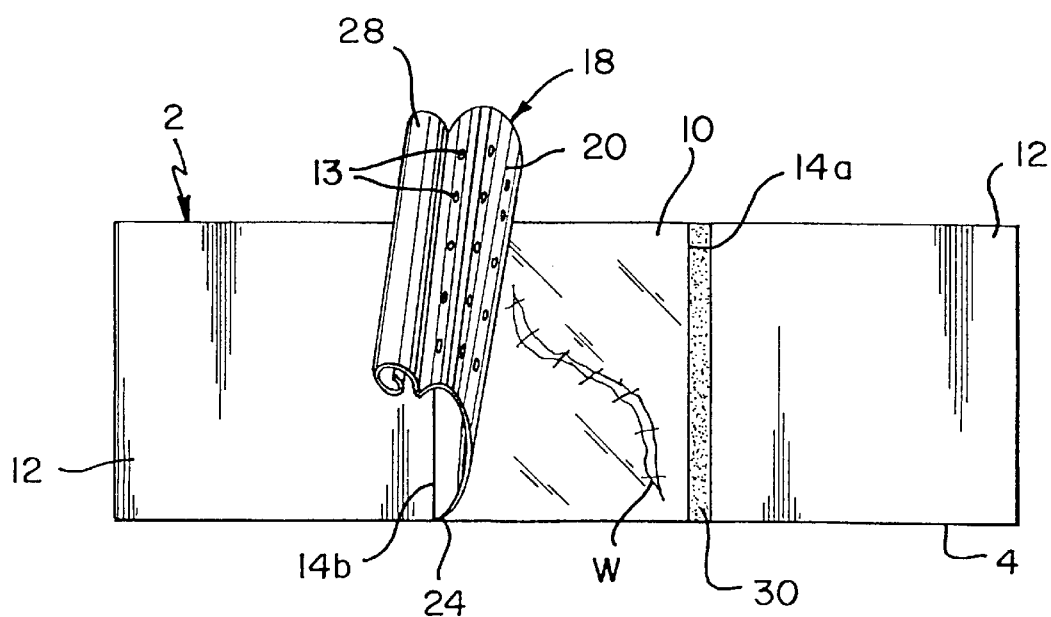
FIG. 2 is a plan view of the embodiment of the invention shown in FIG. 1 rotated 180°.
Figure 3:
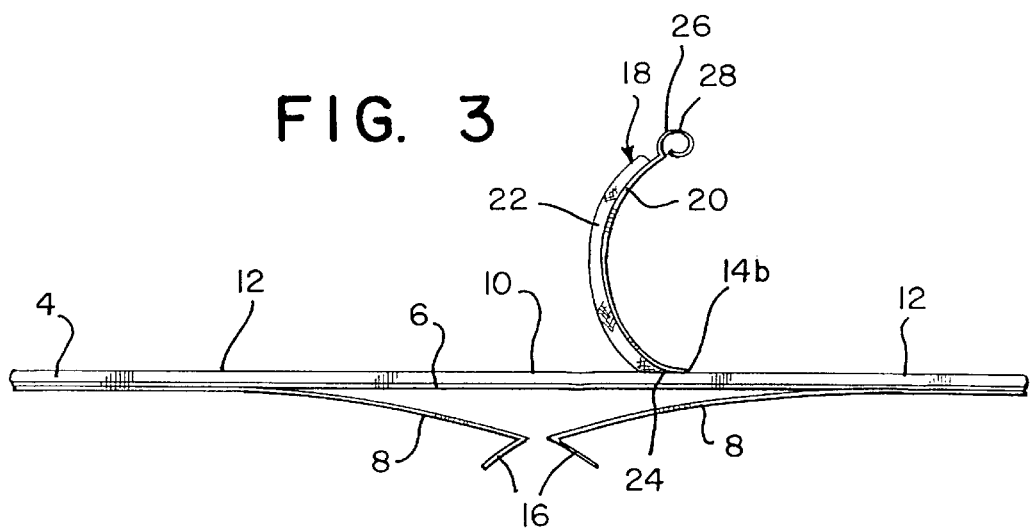
FIG. 3 is a side view of the embodiment shown in FIG. 1.

Referring to FIGS. 1–3, there is shown a first embodiment of the wound dressing of the present invention particularly adapted for covering superficial wounds and abrasions such as those typically covered by Band-Aid® brand wound dressings. The wound dressing 2 includes a layer of backing sheet material 4 having an adhesive 6 on the bottom surface thereof and a release paper 8 (see FIG. 3) releasably attached to the adhesive 6.

The backing sheet material 4 has a first portion 10 which is intended to be positioned directly over the wound identified by the letter "W". In accordance with one aspect of the present invention, the first portion 10 of the backing sheet material 4 enables a person to view the wound without removing the wound dressing 2.

The first portion 10 of the backing sheet material 4 may be transparent or may comprise a cut-out portion or opening as discussed hereinafter in connection with FIG. 6. The transparent first portion 10 as shown in FIGS. 1–3 may be made of such known materials as a transparent polyurethane film of about 0.5 to 2 mils (13 to 51 microns) which may or may not be permeable to gases and/or liquids as identified in Johns, U.S. Pat. No. 4,513,739, and Hodgson, U.S. Pat. No. 3,645,835, incorporated herein by reference. Permeability may be imparted to the polyurethane film by providing a plurality of spaced apart perforations through the film as shown by numeral 11. Alternatively, the first portion 10 may be made of a mesh type material which enables at least partial viewing of the wound.

The backing sheet material 4 has a second portion 12 extending outwardly on both ends 14a, 14b of the first portion 10. The second portion 12 may be made of the same material as the first portion or may be made of more traditional opaque materials which are two-way stretchable, non-toxic, and porous. Examples of such materials are Nylon, Dacron, polyethylene, cotton and linen, such as disclosed in N. R. Dibelius, U.S. Pat. No. 3,367,329, incorporated herein by reference.

The backing sheet material 4 is attached to the skin through an adhesive layer 6. The adhesives which may be used may be any conventional adhesive which is non-toxic and readily adheres to the skin. One such example is disclosed in S. M. Cole, U.S. Pat. No. 5,009,224, incorporated herein by reference, which discloses a pressure-sensitive adhesive having a discontinuous gaseous phase.

The adhesive layer 6 is covered with a release paper 8 which will protect the adhesive during storage of the wound dressing and be easily released therefrom when the wound dressing is to be placed over the wound. The release paper 8 may be any sheet material having these properties such as paper, polyethylene and polypropylene. A suitable release material, for example, is a 40 to 75 pound basis weight paper coated on one or both sides with a suitable finish such as clay and with a release agent such as silicone. The thickness of the release layer 8 will normally be about 2 to 6 mils (51 to 152 microns). A pull tab 16 may be attached to the release layer 8 as shown best in FIG. 3. Other types and arrangements of release paper 8 may be found in O. L. John, U.S. Pat. No. 4,513,739.

In accordance with the present invention, the first portion 10 of the backing sheet material 4 is covered with a flap 18 which is movable from an open position as shown in FIGS. 1–3 wherein the first portion 10 of the backing sheet material 4 is exposed, to a closed position (not shown) covering the first portion 10 of the backing sheet material 4.

The flap 18 is comprised of a backing material 20 which may be the same material used for the second portion 12 of the backing sheet material 4. As shown in FIG. 2, the flap 18 may optionally include perforations 13 to impart permeability as described above for the transparent film shown in FIG. 1. The flap 18 may optionally include a layer of gauze 22 (see FIG. 3) which adheres to the backing material 20 by a conventional adhesive. Adhesives exemplified for use with the underside of the backing sheet material 4, previously described, may be used for this purpose.

The flap 18 has a first end 24 either permanently or removably attached to the backing sheet material 4 at the end 14b of the first portion 10. Attachment may be by use of an adhesive, by hot pressing, stitching or other suitable means. The opposed end 26 has a surface 28 which contacts a corresponding surface 30 of the backing material 4 located at the end 14a of the first portion 10 when the flap 18 is moved to the closed position. Either of the surfaces 28 and 30 may be provided with a suitable adhesive or other means of releasable attachment such as a loop and hook fabric sold under the trademark VELCRO.

If the flap 18 is attached permanently to the end 14b of the backing sheet material 4, the flap 18 can be pivoted about the end 14b to expose or cover the wound. Flap 18 may include a tab at its free end for reversibly moving the flap from the open to the closed position. Alternatively, if the flap 18 is only temporarily attached at the ends 14a and 14b, the flap may be lifted upwards from the backing sheet material 4 to expose the wound and then again placed into contact with the backing sheet material 4 to cover the wound. In this embodiment of the invention, the same flap 18 may be placed over the wound or an entirely new flap may be placed over the wound.

In operation, the wound dressing 2 of the present invention is placed upon the wound "W" in the same manner as other typical wound dressings. Specifically, the release paper 8 is removed from the adhesive 6 by pulling on the respective pull tabs 16. The wound dressing 2 is then pressed against the skin so that the second portion 12 of the backing material adheres to the individual while the first portion 10 covers the wound.

In order to view the wound without removing the wound dressing, the flap 18 is pulled upwardly so that the respective surfaces 28 and 30 disengage from each other and the wound beneath the flap 18 is exposed if the flap 18 is permanently attached to the end 14b. Alternatively, if the flap 18 is temporarily attached at both ends 14a and 14b, such as by a release type adhesive, the flap 18 may be entirely removed from the backing sheet material 4. When viewing of the wound is no longer desired, the flap 18 is moved downwardly by the user until the surfaces 28 and 30 are reengaged and the flap 18 thereby covers the wound. Alternatively, the flap 18 is again placed over the wound so that the cover is reengaged at both ends 14a and 14b.

Figure 4:
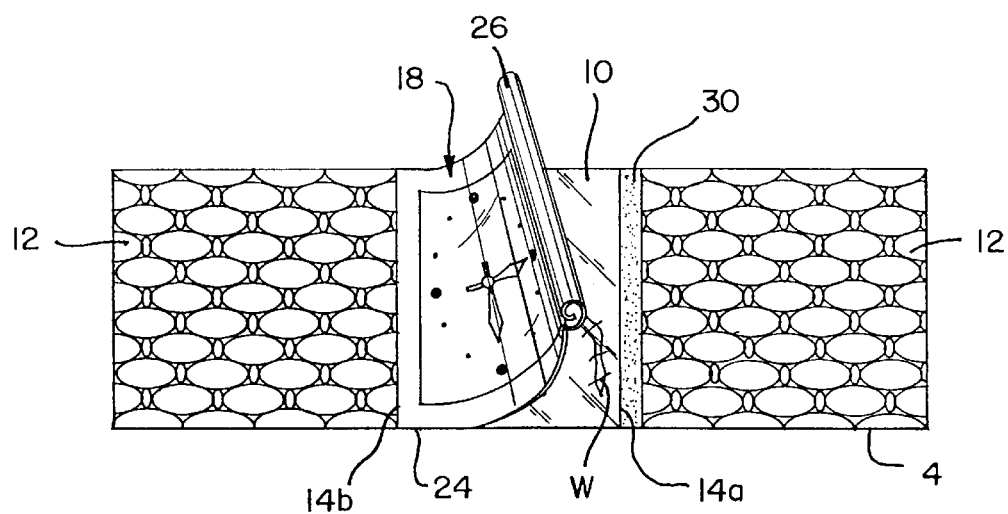
FIG. 4 is another embodiment of the present invention similar to FIG. 1 in which the upper surfaces of the wound dressing are imprinted with indicia.

The wound dressing of the present invention may be decorated with various designs and/or illustrations, particularly for younger children. One such example is shown in FIG. 4. The upper surface of the second portion 12 of the sheet backing material 4 has a design in the form of a watch band while the upper surface of the flap 18 is decorated with a watch face.

Figure 5:
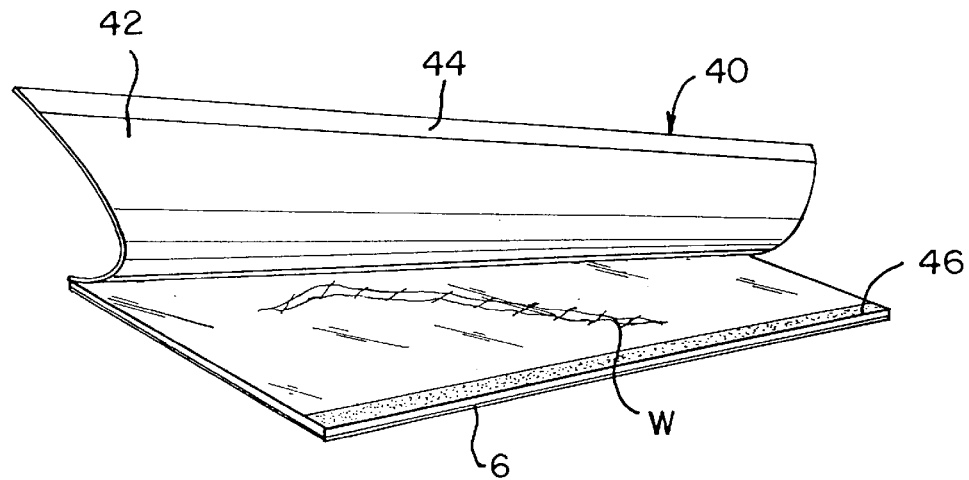
FIG. 5 is a perspective view of another embodiment of the wound dressing of the present invention which is adapted for covering large surgical wounds.

The wound dressing of the present invention may be made in a variety of shapes and sizes within the spirit and scope of the invention. For example, referring to FIG. 5, there is shown a large surgical bandage used for covering major surgical wounds such as encountered with chest surgery. The wound dressing 40 has a flap 42 which is attached along one end of the length of the wound dressing to facilitate moving the flap from the open to the closed position. The end 44 of the flap 42 is adapted to reversibly engage a corresponding end 46 to cover the wound when the flap 42 is pushed downwardly over the wound.

In another embodiment of the invention, the first portion of the backing sheet material comprises an opening in the backing sheet material 4. The flap is, like the embodiments of the invention previously described, reversibly movable to an open from a closed position to expose and cover the wound, respectively.

Figure 6:
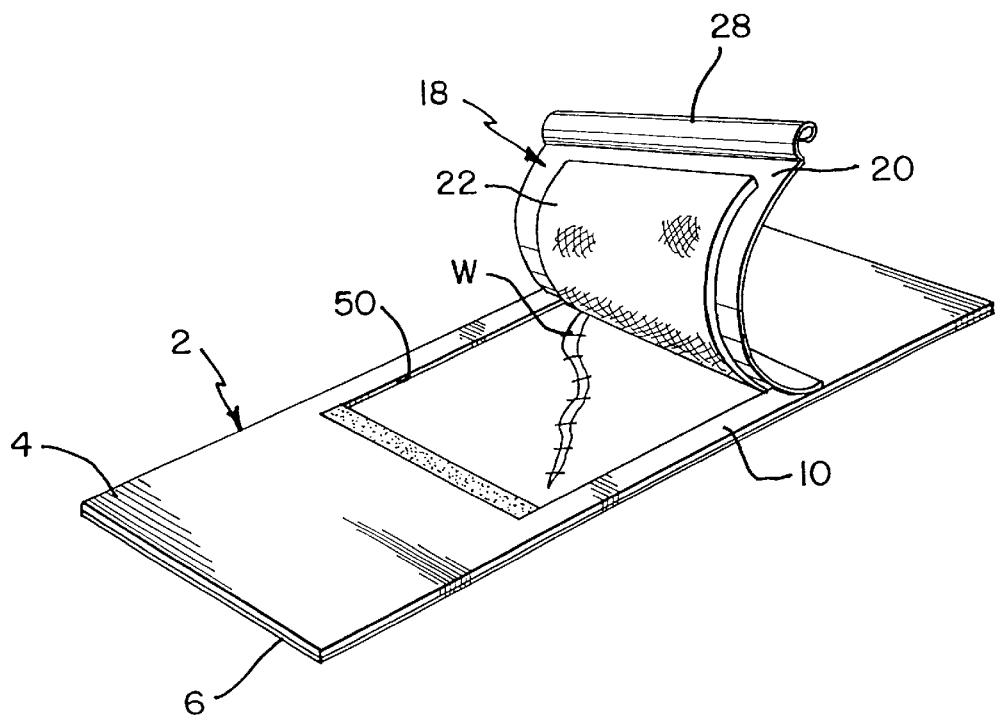
FIG. 6 is a perspective view of still another embodiment of the invention in which the backing layer which adheres to the skin has a cut-out portion exposing the wound.

Referring specifically to FIG. 6, the wound dressing 2 has a first portion 10 comprising an opening 50 directly over the wound W. The wound dressing includes a flap 18 like the previously described embodiments which is adapted to cover the wound. In this embodiment, the flap 18 provides the sole protection for the wound.

Other modifications of the invention would be apparent to those of ordinary skill in the art. For example, the wound dressing may be provided with a customary antibacterial agent by impregnating the same in the first portion 10 of the backing sheet material 4 and/or the gauze 22 on the underside of the flap 18.

I claim:

1. An external wound dressing comprising:
   (a) layer of backing sheet material having a first portion in the form of an opening for positioning over the wound and a second portion, said first portion having a first end and a second end, and said second portion having a first face and a second face;
   (b) an adhesive on said first face of said second portion of said layer of backing sheet material, said adhesive being selected for ready adherence to the skin of a patient to thereby adhere said layer of backing sheet material to the skin of the patient;
   (c) a flap comprising a layer of backing material, said backing material layer having a first end and a second free end, wherein said second free end is defined by an unencumbered edge of backing material free from connection to additional backing material, said first end of said backing material layer being coupled to said second portion of said layer of backing sheet material at said first end of said first portion of said layer of backing sheet material; and
   (d) a releasable attachment element on said second end of said backing material layer, said attachment element permitting repeated releasing and reattaching of said second end of said backing material layer directly to said second face of said second portion of said layer of backing sheet material at said second end of said first portion of said layer of backing sheet material such that said flap is movable from a closed position covering the wound to an open position so that the wound can be selectively viewed by the user.

2. The external wound dressing of claim 1, wherein said first end of said backing material layer is permanently attached directly to said layer of backing sheet material such that release and reattachment is not permitted and said second end is releasably attached directly said layer of backing sheet material to permit repeated opening and closing of said flap.

3. The external wound dressing of claim 2, wherein said first end of said backing material layer is attached to said layer of backing sheet material with an adhesive.

4. The external wound dressing of claim 2, wherein said first end of said backing material layer is attached to said layer of backing sheet material by hot pressing.

5. The external wound dressing of claim 2, wherein said first end of said backing material layer is attached to said layer of backing sheet material by stitching.

6. The external wound dressing of claim 1, wherein said first end and said second end of said backing material layer are releasably attached directly to said layer of backing sheet material to permit repeated attachment and removal of the entire flap to and from said layer of backing sheet material.

7. The external wound dressing of claim 1, wherein said releasable attachment element on said second end of said backing material layer is an adhesive.

8. The external wound dressing of claim 1, wherein said flap further includes a gauze material adhered to said flap and facing the wound.

9. The external wound dressing of claim 8, further comprising an antibacterial agent impregnated in said gauze material of said flap.

10. The external wound dressing of claim 1, further comprising a tab at one end of said flap for reversibly moving said flap from the open to the closed position.

11. The external wound dressing of claim 1, further comprising a layer of protective sheet material covering said adhesive on said layer of backing sheet material, said layer being removable from said adhesive to enable said wound dressing to be applied to the wound.

12. The external wound dressing of claim 1, wherein said releasable attachment element is a hook and loop fabric.

13. The external wound dressing of claim 1, wherein said backing sheet material is a film.

14. The external wound dressing of claim 13, wherein said film is a polyurethane film.

15. The external wound dressing of claim 1, wherein said layer of backing sheet material is formed from a two-way stretchable material.

16. The external wound dressing of claim 15, wherein said layer of backing sheet material is formed from a non-toxic, porous material.

17. The external wound dressing of claim 1, wherein said layer of backing sheet material is formed from a non-toxic, porous material.

18. The external wound dressing of claim 1, wherein said layer of backing sheet material is formed from a non-rigid, flexible fabric.

19. The external wound dressing of claim 18, wherein said fabric is selected from the group consisting of nylon, Dacron, polyethylene, cotton and linen.

20. The external wound dressing of claim 1, wherein said backing sheet material is opaque.

21. The external wound dressing of claim 1, wherein said layer of backing sheet material and said flap are decorated with a design.

22. The external wound dressing of claim 1, wherein said flap is formed from the same material as said layer of backing sheet material.

23. The external wound dressing of claim 4, wherein said flap is formed from a material as said backing sheet material.

24. The external wound dressing of claim 1, wherein said flap is opaque.

25. An external wound dressing for selectively covering and uncovering a wound, said wound dressing comprising:
   a layer of backing sheet material positioned on both sides of the wound and leaving an opening over the wound, said layer of backing sheet material having a first face and a second face;
   an adhesive on said first face of said layer of backing sheet material, said adhesive being selected for ready adherence to the skin of a patient to thereby adhere said wound dressing to the skin of the patient;
   a flap formed from a layer of backing material separate from said backing sheet material and having a first end and a second end, said first end of said flap being coupled to said first layer of backing sheet material on one side of the wound; and a releasable attachment element on said second end of said flap, said attachment element permitting repeated releasing and reattaching of said second end of said flap directly to said second face of said layer of backing sheet material on the other side of the wound such that said flap is movable from a closed position covering the wound to an open position uncovering the wound.

26. The external wound dressing of claim 25, further comprising a sheet of release paper covering said adhesive on said layer of backing sheet material, said release paper being removable from said adhesive to enable said wound dressing to be applied to the wound.

27. The external wound dressing of claim 25, wherein said backing sheet material is a film.

28. The external wound dressing of claim 25, wherein said backing sheet material is a two-way stretchable material.

29. The external wound dressing of claim 28, wherein said backing sheet material is a non-toxic, porous material.

30. The external wound dressing of claim 25, wherein said backing sheet material is a non-rigid, flexible fabric.

31. The external wound dressing of claim 25, wherein said flap is formed from the same material as said backing sheet material.

32. The external wound dressing of claim 25, wherein said flap is formed from a material different from said backing sheet material.

33. The external wound dressing of claim 25, wherein said flap is opaque.

* * * * *